United States Patent [19]

Wong

[11] Patent Number: 5,658,736
[45] Date of Patent: Aug. 19, 1997

[54] OLIGONUCLEOTIDE POPULATION PREPARATION

[75] Inventor: Gordon G. Wong, Brookline, Mass.

[73] Assignee: Genetics Institute, Inc., Cambridge, Mass.

[21] Appl. No.: 586,329

[22] Filed: Jan. 16, 1996

[51] Int. Cl.$^6$ ............................. C12Q 1/68; C07H 21/04
[52] U.S. Cl. ..................... 435/6; 536/24.2; 536/23.1; 435/91.3
[58] Field of Search ..................... 435/6, 91.1, 91.2, 435/91.4, 91.3; 536/24.3, 23.1

[56] References Cited

U.S. PATENT DOCUMENTS

| | | | |
|---|---|---|---|
| 4,942,124 | 7/1990 | Church | 435/6 |
| 5,149,625 | 9/1992 | Church et al. | 435/6 |
| 5,173,410 | 12/1992 | Ahlquist | 435/91 |

OTHER PUBLICATIONS

Velculescu et al, Science 270:484–487 (1995).
Szybalski et al., Gene 100:13–26 (1991).
Jarvik et al. (1996) BioTechniques 20:896–904.
Church et al. (1988) Science 240:185–240.

*Primary Examiner*—W. Gary Jones
*Assistant Examiner*—Amy Atzel
*Attorney, Agent, or Firm*—Scott A. Brown; Thomas J. DesRosier

[57] ABSTRACT

Methods are disclosed for producing a sequence tag from a polynucleotide. In preferred embodiments, the method comprises (a) digesting the polynucleotide with a type II restriction enzyme to produce a first cohesive end; (b) providing a promoter-linker cassette comprising an RNA polymerase promoter, a restriction site for a type IIS restriction enzyme and a second cohesive end which is complementary to the first cohesive end produced by the type II restriction enzyme; (c) ligating the digested polynucleotide to the cassette by joining the first cohesive end and the second cohesive end; (d) digesting the ligated product of step (c) with the type IIs restriction enzyme; and (e) transcribing the resulting construct from the promoter thereby producing a sequence tagged polyribonucleotide.

17 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

```
TAATACGACT  ACTATAGGGA  CATG                                         24
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

```
TCCCTATAGT  AGTCGTATTA                                               20
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

```
ATAGGGACAT  GNNNNNNNNN  NN                                           22
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: other nucleic acid (x i) SEQUENCE DESCRIPTION: SEQ ID NO:4:

NNNNNNNNNC ATGTCCCTAT                              20

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:5:

CCCCCTATAG TGAGTCGTAT TAGGATG                      27

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:6:

GATCCATCCT AATACGACTC ACTATAGGGG G                 31

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:7:

ATTAGGATGG ATCNNNNN                                18

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:8:

NNNNNNNNNG ATCCATCCTA AT                           22

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:9:

```
GATCNNNNNN NNNCCC                                                                                          16
```

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

```
ATTAGGATG                                                                                                  9
```

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

```
GATCCATCCT AAT                                                                                            13
```

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

```
GGGNNNNNNN NN                                                                                             12
```

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

```
GGGGGNNNNN NNNNGATC                                                                                       18
```

OLIGONUCLEOTIDE POPULATION PREPARATION

FIELD OF INVENTION

The present invention relates to preparation of a population of polynucleotide sequences for analysis by hybridization or sequencing. Particularly, the invention provides methods for reducing the complexity of polynucleotide samples for analysis. The disclosed methods are particularly useful for preparing samples for analysis by hybridization of representative short defined length RNA or DNA oligonucleotides to an array (or other presentation means) of mobilized polynucleotide (e.g., DNA or RNA) sequences.

BACKGROUND OF THE INVENTION

Many investigators are presently working on the problem of identifying and quantifying the concentration of specific genes or polynucleotide sequences within a larger population of sequences. As an example, consider the problem of measuring for the presence and concentration of actin gene mRNA transcripts in a cell's RNA population, or the concentration of the actin cDNA gene in a population of cDNA molecules, or the identity and concentration of the actin gene in a genome. The problem becomes more complex when one wants to measure not only the actin gene but rather to identify and quantify every possible gene or genetic sequence in the population. The population could be immensely complex and have on the order of $10^5$ different (i.e., distinct) DNA sequences. RNA populations can be dealt with by convening to a cDNA population using oligo dT primers or random primers. Then the RNA problem becomes effectively the same as the DNA problem.

Typically, the length of each polynucleotide sequence is from $10^2$ to $10^4$ bases in length—probably with a mean of about $10^3$ bases. The number of different sequences in a cell's mRNA population is likely to be less than $10^5$ (the estimated number of genes), but in about the $10^4$ range. The typical case would be a population of about $10^4$ different DNA sequences with each sequence being about $10^3$ bases long. However, the complexity of a particular polynucleotide population may actually be much higher.

Strategies have been suggested to provide less cumbersome ways to analyze these large populations of polynucleotides. For example, Velculescu et al., Science 270, 484, 1995, propose a regimen for serial analysis of gene expression (or "SAGE"). SAGE allows the construction of a more uniform population of unique polynucleotides from the larger population which is to be analyzed. SAGE employs a combination of a "sampling" restriction enzyme (having a 4 bp recognition site) and a "tagging" restriction enzyme (a type IIs restriction enzyme) to produce unique 13-base tags (a 4-base common sequence combined with a 9-base variable unique sequence) from each polynucleotide in the population under analysis. These tags are then concatamerized and sequenced to determine the identity of the tags. The sequenced tags can then be compared with known sequences to determine which gene or sequences were in the analyzed population. However, the SAGE technology is still a very cumbersome process. Sequence analysis of the thousands concatamerized tags can be a labor- and resource intensive process, thus limiting the applicability of the process where speed and ease of analysis is desirable or required.

Therefore, it would be desirable to provide more efficient and improved methods for decreasing the complexity of a polynucleotide population which is to be analyzed. It is also desirable to provide methods for characterizing a population of polynucleotides by sampling only part of each polynucleotide. It would also be desirable to provide methods for producing unique sequence tags from a large population under analysis and to provide efficient methods for analysis of such tags.

SUMMARY OF THE INVENTION

In accordance with the present invention, methods are provided for producing a unique sequence tag from a polynucleotide, said method comprising:

(a) digesting said polynucleotide with a type II restriction enzyme;

(b) providing a promoter-linker cassette comprising a polymerase promoter, a restriction site for a type IIs restriction enzyme and a cohesive end complementary to cohesive ends produced by said type II restriction enzyme;

(c) ligating the digested polynucleotide to the cassette;

(d) digesting the ligated product of step (c) with said type IIs restriction enzyme; and (e) transcribing the resulting construct.

Methods are also provided for analyzing a population of polynucleotides. Such methods comprise:

(a) producing unique sequence tags from said polynucleotides according to the method for producing unique sequence tags from polynucleotides described above; and (b) hybridizing said tags to one or more oligonucleotides of known sequence.

In preferred embodiments, the said cassette further comprises a clamp sequence at the 5' end of said promoter.

In other embodiments, methods are provided for producing a unique sequence tag from a polynucleotide, said method comprising:

(a) digesting said polynucleotide with a type II restriction enzyme;

(b) providing a promoter-linker cassette comprising a polymerase promoter, a restriction site for a type IIs restriction enzyme and a cohesive end complementary to cohesive ends produced by said type II restriction enzyme;

(c) ligating the digested polynucleotide to the cassette;

(d) digesting the ligated product of step (c) with said type IIs restriction enzyme;

(e) circularizing the product of step (d);

(f) digesting the circularized product with said type II restriction enzyme; and (g) transcribing the resulting construct.

Other embodiments provide for a method for producing a unique sequence tag from a polynucleotide which comprises:

(a) shearing the polynucleotide;

(b) providing a promoter-linker cassette comprising a polymerase promoter and a restriction site for a type IIs restriction enzyme;

(c) ligating the sheared polynucleotide to the digested cassette;

(d) digesting the ligated product of step (c) with the type IIs restriction enzyme; and (e) transcribing the resulting construct.

In certain preferred embodiments, the cassette may contain the polymerase promoter, the type IIs restriction site and a site for a type II restriction enzyme which produces ends cohesive with those produced by the type II enzyme used to digest the polynucleotides population under analysis. In such embodiments, the cassette is digested to produce cohesive ends prior to combination with the digested polynucleotides. In other preferred embodiments, the ends of the product of the type IIs digestion are blunted prior to circularization and/or transcription.

In particularly preferred embodiments, the type II restriction enzyme is selected from the group consisting of an enzyme having a 4-base recognition site, an enzyme having a 5-base recognition site and an enzyme having a 6-base recognition site. In other particularly preferred embodiments, the type IIs restriction enzymes is selected from the group consisting of HphI, MboII, BbvI, FokI, HgaI, SfaNI, BspMI, BsmF1, MnlI, AlwI, AlwXI, Alw26I, BbsI, BbvII, BcefI, BccI, BcgI, BinI, BsaI, BsgI, BsmAI, EarI, Eco31I, Eco57I, Esp3I, FauI, GsuI, HinGUII, Ksp632I, MmeI, NgoVIII, PleI, RleAI, SapI, TaqII and Tth 111II.

In other preferred embodiments, the transcribing step is performed using an RNA polymerase. Preferably the polymerase is selected from the group consisting of T7 polymerase, T3 polymerase and Sp6 polymerase.

In still other embodiments, the invention provides a method for producing a unique sequence tag from a polynucleotide, said method comprising:

(a) digesting said polynucleotide with a type II restriction enzyme;

(b) ligating the digested polynucleotide to a promoter-linker cassette comprising a polymerase promoter and a cohesive end complementary to cohesive ends produced by said type II restriction enzyme, such that the ligated product contains a recognition site for a type IIs restriction enzyme;

(c) digesting the ligated product of step (b) with said type IIs restriction enzyme; and (d) transcribing the resulting construct.

In certain preferred embodiments, the recognition site for the type IIs restriction enzyme is formed upon ligation.

The present invention also provides a promoter-linker cassette comprising a polymerase promoter, a restriction site for a type IIs restriction enzyme and a restriction site for a type II restriction enzyme.

DETAILED DESCRIPTION

The present invention overcomes many of the inefficiencies and undesirable features of prior art methods by generating short DNA or RNA oligonucleotide tags that are representative of a more complex population of DNA or RNA molecules. Consider that the average cell has about 400,000 mRNA molecules (sequences), each sequence being on average about 1,000 bases long. Most of these mRNAs, can be converted to double stranded cDNA by standard methods. The base composition and order in any particular polynucleotide sequence provide inherent information concerning its unique identity. One goal of the present invention is to be able to uniquely identify and quantify each molecule within this population.

For an oligonucleotide composed of bases A, T, G and C that is four bases in length, there are 256 possible sequences; for 10 bases, about $1.05 \times 10^6$; for 15 bases, about $1.07 \times 10^9$; for 18 bases, about $7 \times 10^{10}$. Thus, there are conceivably more possible 15-base oligonucleotides than are present in the cellular population of 400,000 DNA molecules (each averaging about 1,000 bases). Therefore, one can theoretically uniquely identify each DNA molecule (or sequence of oligonucleotide) by a unique 15mer oligonucleotide intrinsic to the molecule's sequence. Of course, in cells DNA molecules could share regions of homology which would impede complete unique identification. Nevertheless, providing a small number of 15mer (or longer) sequences from each molecule in the population substantially decreases the complexity of the sample which needs to be analyzed. In the ideal, each unique DNA sequence could be represented by a single 15mer sequence. The present invention provides advantages over methods of the prior art by generating a specific (or small set) 15mer (or longer) oligonucleotides from every polynucleotide molecule (sequence) in a population and the analyzing the composition and distribution of the resulting oligonucleotides. By limiting the number of oligonucleotides generated from each polynucleotide molecule (sequence), one reduces the complexity of the sequence information being analyzed from the entire population of sequences.

A variation of this strategy has been developed by Velculescu et al., Science (1995) for identifying and measuring gene expression. To ensure that every cDNA sequence of a mRNA population is sampled, Velculescu et al. use a 4 cutter; however, a 4 cutter will sample 4 sites on average per $10^3$ base pair sequence. To reduce this complexity, Velculescu et al. limited the analysis to the first 4 base cutter site at the 3' end of the cDNA, by using a biotinylated oligo dT primer. The complexity could also be reduced by using a 5 or 6 base pair cutter restriction site. Of course, the restriction site may not occur in the sequence of interest; however, since all gene sequences will eventually be available, the appropriate set of 5 and/or 6 base pair recognition restriction enzymes can be chosen so that all possible sequences are sampled. However, the methods of Velculescu et al. still require cumbersome concatamerization and sequencing steps to analyze the oligonucleotides produced.

The present invention provides methods for efficiently analyzing unique polynucleotides. In preferred embodiments, a promoter-linker cassette of the following general structure:

The cassette contains the T7 polymerase promoter ligated to a linker containing a type IIs restriction site, which is in turn ligated to a linker containing a type II restriction site (for the sampling enzyme) (preferably the type II enzyme has a 4, 5 or 6 base recognition sequence). This cassette can be optionally provided with means for its isolation from a sample. For example, it may be biotinylated for separation using streptavidin or other means.

Other RNA polymerase promoters may be substituted for the T7 promoter in the promoter-linker cassette. Other transcription promoters can also be used, with their corresponding polymerase being substituted for RNA polymerase. Suitable substitute promoter include without limitation the T3 and Sp6 promoters.

Any type IIs restriction site can be used in forming the promoter-linker cassette. Type IIs restriction endonucleases recognize specific, generally palindromic DNA sequences and cleave the DNA at a point remote from the recognition site to leave either a symmetrical blunt cleavage across the DNA recognition site or an asymmetrical 5' or 3' overhang. The length of the overhang, where one is produced, ranges from 1 to 5 bases. The recognition site is either 4, 5, 6 or 8 base pairs in length in general. Szybalski et al., Gene 100:13, 1991, reviews numerous type IIs restriction enzymes, their recognition sites and their cutting patterns. Each of the enzymes disclosed therein is suitable for practicing the present invention. Some examples of type IIs restriction enzymes include without limitation those listed in Table 1.

TABLE 1

| | |
|---|---|
| HphI | GGTGAN$_8$ ↓ |
| | CCACTN$_7$ ↑ |
| MboII | GAAGAN$_8$ ↓ |
| | CTTCTN$_7$ ↑ |
| BbvI | GCAGCN$_8$ ↓ |
| | CGTCGN$_{12}$ ↑ |
| FokI | GGATGN$_9$ ↓ |
| | CCTACN$_{13}$ ↑ |
| HgaI | GACGCN$_5$ ↓ |
| | CTGCGN$_{10}$ ↑ |
| SfaNI | GCATCN$_5$ ↓ |
| | CGTAGN$_9$ ↑ |
| BspMI | ACCTGCN$_4$ ↓ |
| | TGGACGN$_8$ ↑ |
| BsmF1 | GGGACN$_{10}$ ↓ |
| | CCCTGN$_{14}$ ↑ |
| MnlI | CCTCN$_7$ ↓ |
| | GGAGN$_7$ ↑ |

Any type II restriction enzyme can be used in the promoter-linker cassette as the sampling enzyme. Enzymes having 4, 5 or 6 base recognition sequences are preferred. The use of enzymes having different length recognition sites will allow different sampling of the sample population. With the longer base recognition sites, less of the population is sampled, but more "selective amplification" is provided. For example, a 6-base cutter will cleave DNA at random an average of every 4,096 bases, but will select a different set of sequences.

As used herein "type II restriction enzyme" excludes type IIs restriction enzymes. Sites of 4 bases are preferred because they allow some confidence that virtually all polynucleotides in a population under analysis will be cut and made available for attachment to the cassette. Suitable type II restriction enzymes (including without limitation 4, 5 and 6 base restriction enzymes) are known to those skilled in the art.

Restriction sites for enzymes used in practicing the present invention can also be constructed in situ upon the ligation of components of the cassette to each other or of the oligonucleotide joined to the cassette. For example, the type IIs restriction site can be created by the ligation of a cassette of appropriate sequence to a population of oligonucleotides such that the ligated junction forms the necessary type IIs site.

Cassettes for practicing the present invention can be constructed by any biological or synthetic method providing the desired product. Appropriate cassettes can be produced by digestion and ligation of appropriate sequences from available sources or can be constructed by hybridization of synthesized oligonucleotides.

Cassettes may also be constructed to include other useful elements. For example, means may be incorporated into the cassette to assist in isolation of the unique oligonucleotide or the oligonucleotide/cassette combination produced in accordance with the present invention. Examples of such means include without limitation recombinase recognition sequences (such as Cre/lox).

To analyze a population of polynucleotides in accordance with the present invention, the population is first treated with the sampling enzyme (preferably to complete digestion). The resulting digested sampled is then combined with the promoter-linker cassette, which has also been treated with the sampling enzyme or has been constructed to have ends cohesive with those of the digested sample. The mixture is then ligated to join the sample DNA and cassette. The resultant sample is then digested with the type IIs restriction enzyme to produce a unique sequence tag. After optionally filling in or blunting the uneven end of the resulting constructs, the T7 promoter can be used to produce transcripts for analysis from the sequence downstream from the promoter.

The resulting transcripts are then analyzed, usually by hybridization to oligonucleotides of known sequence. Methods of analysis include, without limitation, hybridization of the sample to an array of oligonucleotides on a solid support (such as, for example, an array on a "DNA chip"); running the sample on a gel; running the sample on a gel, then blotting and probing for target sequences; and using the sample to pull out complementary RNA or DNA sequences in another source (e.g., a substraction hybridization scheme). Analysis of the sequence of each tag could also be determined and analyzed by conventional nucleotide sequencing or by employing chain terminating nucleotides in the transcription step to generate different length oligonucleotides, which can in turn be analyzed. Other methods for analysis are known in the art.

The hybridization analysis can be performed by any means in which specific hybridization to the known sequences can be detected. Preferably the known oligonucleotides are anchored to a solid support which allows one to infer the sequence of the sample DNA from the position of the oligonucleotide to which it binds on the solid support. For example, arrays of oligonucleotides are particularly preferred in which an oligonucleotide of a particular sequence is placed at a particular identifiable position on the array. In such embodiments, the presence of a particular sequence in the sample can be inferred by the detection of hybridization to its complement at a particular position in the array.

In one exemplary method, cDNA is made from a sample of RNA with biotinylated oligo dT and converted to double stranded cDNA by standard methods. The cDNA is treated with 4 base pair cutter NlaIII, that leaves a 4 base pair 3' overhang. The Nla III cut cDNA is passed over a streptavidin magnetic had system to recover the 3' end of cDNAs separate from the remaining cDNA population. The uncovered 3' end cDNA is ligated to the DNA shown below which contains the T7 promoter (Martin et al., Biochemistry 26, 2690, 1987), a type IIs restriction site for BsmF1 and a sticky end from a NlaIII site. The 3'-terminal A of the shorter strand of this promoter-linker cassette is a dideoxy residue which prevents concatamerization during subsequent ligation steps.

5' TAATACGACTACTATA GGGACATG
3' ATTATGCTGATGATAT CCCT

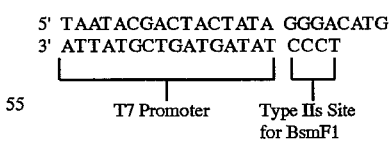

(SEQ ID NO: 1 and SEQ ID NO: 2, respectively)

After ligating, the resulting constructs are cleaved with the IIs enzyme, BsmF1. With BsmF1, and the sequence of the oligonucleotides to be ligated expect BsmF1, to cut at 37° C. at 14/12 bp 3' of the BsmF1 site, at 65° C. at 16/14 bp 3' of the BsmF1 site. At 37° C., the following would be produced:

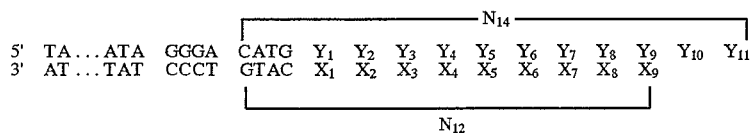

(SEQ ID NO: 3 and SEQ ID NO: 4, respectively) The resulting DNAs are treated with DNA polymerase, or T4 polymerase to achieve a blunt end.

In this example, the length of DNA adjacent to the sampling restriction enzyme site, e.g., the 4 bp cutter is 9 base pairs (the length of the 5'→3' strand is irrelevant as the T7 polymerase will use the 3'→5' strand as a template and therefore the length of 3'→5' strand really determines the length of the RNA oligonucleotide to be generated.) The length of RNA oligo generated will be 5+3+9=17 bases; 5 bases from the IIs site, 3 bases from the 4 base restriction sight, and 9 bases adjacent to the 4 base pair restriction site.

Depending on the IIs used, the sampling restriction enzyme used and whether additional nucleotides are inserted between the T7 polymerase start site, and the IIs and the complimentary bases for attachment, the length of n bases that will vary. The sequence composition and order of the n bases is what will determine identities.

If the following oligonucleotides are used

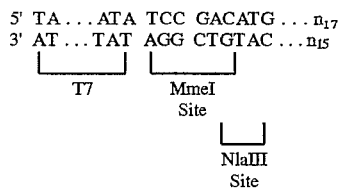

and treated with MmeI, then the variable region will be n=15 bases, and the length of the T7 transcript generated will be 24 bases.

The optimum arrangement will be to have at least n=9 bases of sequence (because of the $4^9$ sequence complexity) and to have the T7 promoter sequence such that a transcript of about 15–25 base pairs is synthesized. The following equation is useful in deciding how to construct appropriate promoter-linker cassettes for producing transcripts of the desired length: $N=C_n+n$, where N is the total length of the resulting transcripts; $C_n$ is the number of nucleotides provided by the remnant of the type IIs site, the sampling enzyme site and any additional bases included in the constant region of the cassette; and n is the number of unique bases derived from the sample population. Preferably, N=15–25 (more preferably N=18) and n>9 (more preferably n=9).

In another example, transcripts are produced which have constant regions at both ends of the unique variable region derived from the sample. For unambiguous identification of DNA sequence by hybridization, it would be useful to have the DNA sequence in question to be flanked by two constant DNA regions to act as a "hybridization clamp". For example, a variable 9 mer sequence could be analyzed by hybridization if it was flanked by two constant region clamps. The clamps should preferably be about 5 bases in length, preferably with a high G/C content; however, A/T clamp sequences are also effective.

Using the single clamp method outlined in the above example, by simple modification of the T7 promoter orientation and by inserting some clamp sequences, one can double clamp representative 9 mer sequences (or sequences of other lengths) from a cDNA population.

Biotinylated oligo dT is used to generate double stranded cDNA. the cDNA is treated with Sau3A and the 3' end of the cDNA is recovered and ligated to the oligonucleotides below.

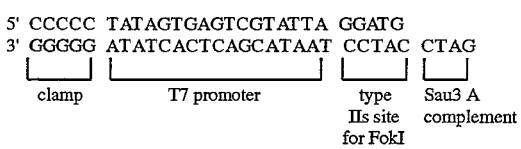

(SEQ ID NO: 5 and SEQ ID NO: 6, respectively) The T7 promoter is in the proper orientation such that it will direct transcription of the clamp region first. This cassette is schematically represented as follows:

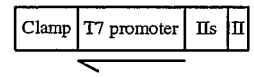

Optionally, an additional clamp sequence can be inserted between the T7 promoter and the IIs recognition site. This promoter-linker cassette is ligated to the Sau3A cut cDNA. The FokI type IIs restriction enzyme is added at 37° C. to generate a 13 base pair cleavage 3' of the Fok1 recognition site.

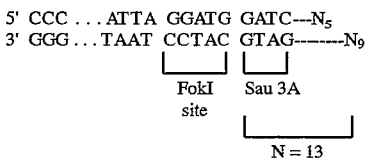

The FokI cut DNA is blunted by T4 polymerase, or DNA polymerase, and then diluted to a concentration so that the DNA molecule self ligates to form a circle.

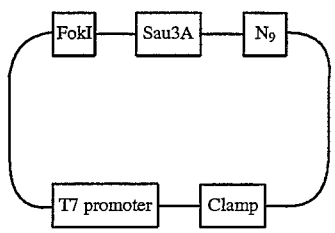

(SEQ ID NO: 7 and SEQ ID NO: 8, respectively) The ligated DNAS are cut with Sau3A, which will linearize the construct and bring the T7 promoter to the other end of the linear DNA molecule to produce the following construct:

5'  GATC---$n_9$---CCC ... ATTAGGATG

```
3'         n9--GGG...TAATCCTACCTAG
```
-continued (SEQ ID NO: 9 and SEQ ID NO: 10; and SEQ ID NO: 11 and SEQ ID NO: 12, respectively) This molecule can be filled in DNA polymerase and then T7 polymerase can be used to generate transcripts having the structure: 5' GGGGG - - - $n_9$ - - - GATC 3', where $n_9$ is the variable sequence. These transcripts can be hybridized to oligonucleotides in an array or on some other solid support, or analyzed by other available methods.

In an alternative method of the present invention, the use of the type II restriction sampling enzyme can be eliminated. Rather than digesting the sample to be analyzed with a type II enzyme, the sample is randomly sheared and ligated to a promoter cassette containing a type IIs restriction enzyme recognition site as described herein. The sheared DNA fragments (preferably sheared to produce fragments of 15–30 bases in length) are ligated to the promoter cassette and the resulting construct is digested with the type IIs enzyme as described to produce tags of an uniform length depending on the enzyme used. The ligated cut oligonucleotides with attached polymerase recognition site is then transcribed as described.

At each step of the methods described herein reacted and unreacted products can, of course, optionally be isolated from unreacted or undesired reaction products in accordance with known methods.

What is claimed is:

1. A method for producing a sequence tag from a polynucleotide, said method comprising:

(a) digesting said polynucleotide with a type II restriction enzyme to produce a first cohesive end;

(b) providing a promoter-linker cassette comprising an RNA polymerase promoter, a restriction site for a type IIs restriction enzyme and a second cohesive end which is complementary to said first cohesive end produced by said type II restriction enzyme;

(c) ligating the digested polynucleotide to the cassette by joining said first cohesive end and said second cohesive end;

(d) digesting the ligated product of step (c) with said type IIs restriction enzyme; and (e) transcribing the resulting construct from said promoter, thereby producing a sequence tagged polyribonucleotide.

2. A method of analyzing a population of polynucleotides for the presence of a known sequence, said method comprising:

(a) producing sequence tags from said polynucleotides according to the method of claim 1;

(b) combining, said tags with one or more oligonucleotides derived from said known sequence; and (c) determining whether said tags hybridize to said one or more oligonucleotides.

3. A promoter-linker cassette oligonucleotide comprising an RNA polymerase promoter which is situated 5' to a restriction site for a type IIS restriction enzyme which is situated 5' to a restriction site for a type II restriction enzyme.

4. A method for producing a sequence tag from a polynucleotide, said method comprising:
   (a) digesting said polynucleotide with a type II restriction enzyme to produce a first cohesive end;
   (b) providing a promoter-linker cassette comprising a polymerase promoter, a restriction site for a type IIs restriction enzyme and a second cohesive end which is complementary to said first cohesive end produced by said type II restriction enzyme;
   (c) ligating the digested polynucleotide to the cassette;
   (d) digesting the ligated product of step (c) with said type IIs restriction enzyme;
   (e) circularizing the product of step (d);
   (f) digesting the circularized product with said type II restriction enzyme; and
   (g) transcribing the resulting construct, thereby producing a sequence tagged polynucleotide.

5. The method of claim 4 wherein said cassette further comprises a clamp sequence at the 5' end of said promoter.

6. The method of claim 1 or 4 wherein said cassette is digested to produce said second cohesive end prior to combination with said polynucleotide.

7. The method of claim 1 or 4 wherein the ends of the product of the type IIs digestion are blunted prior to transcription.

8. The method of claim 4 wherein the ends of the product of the type IIs digestion are blunted prior to circularization.

9. The method of claim 1 or 4 wherein said type II restriction enzyme is selected from the group consisting of an enzyme having a 4-base recognition site, an enzyme having a 5-base recognition site and an enzyme having a 6-base recognition site.

10. The method of claim 1 or 4 wherein said type IIs restriction enzyme is selected from the group consisting of HphI, MboII, BbvI, FokI, HgaI, SfaNI, BspMI, BsmF1, MnlI, AlwI, AlwXI, Alw26I, BbsI, BbvII, BcefI, BccI, BcgI, BinI, BsaI, BsgI, BsmAI, EarI, Eco31I, Eco57I, Esp3I, FauI, GsuI, HinGUII, Ksp632I, MmeI, NgoVIII, PleI, RleAI, SapI, TaqII and Tth111II.

11. The method of claim 1 or 4 wherein the transcribing step is performed by an RNA polymerase.

12. The method of claim 11 wherein said RNA polymerase is selected from the group consisting of T7 polymerase, T3 polymerase and Sp6 polymerase.

13. A method for producing a sequence tag from a polynucleotide, said method comprising:
   (a) shearing said polynucleotide;
   (b) providing a promoter-linker cassette comprising an RNA polymerase promoter and a restriction site for a type IIs restriction enzyme;
   (c) blunting said polynucleotide;
   (d) ligating the sheared polynucleotide to the cassette;
   (e) digesting the ligated product of step (d) with said type IIs restriction enzyme; and
   (f) transcribing the resulting construct from said promoter, thereby producing a sequence tagged polyribonucleotide.

14. A method for producing a unique sequence tag from a polynucleotide, said method comprising:
   (a) digesting said polynucleotide with a type II restriction enzyme;
   (b) ligating the digested polynucleotide to a promoter-linker cassette comprising an RNA polymerase promoter and a cohesive end complementary to cohesive ends produced by said type II restriction enzyme, such that the ligated product contains a recognition site for a type IIs restriction enzyme;
   (c) digesting the ligated product of step (b) with said type IIs restriction enzyme; and
   (d) transcribing the resulting construct from said promoter, thereby producing a sequence tagged polyribonucleotide.

15. The method of claim 14 wherein the recognition site for the type IIs restriction enzyme is formed upon ligation.

16. A method for producing a sequence tag from a polynucleotide, said method comprising:
   (a) digesting said polynucleotide with a type II restriction enzyme to produce a first cohesive end;
   (b) providing a promoter-linker cassette comprising an RNA polymerase promoter, a restriction site for a type IIs restriction enzyme and a second cohesive end which is complementary to said first cohesive end produced by said type II restriction enzyme, wherein said cassette is digested to produce said second cohesive end;
   (c) ligating the digested polynucleotide to the cassette by joining said first cohesive end and said second cohesive end;
   (d) digesting the ligated product of step (c) with said type IIs restriction enzyme;
   (e) blunting the ends of the product of the type IIs digestion; and
   (f) transcribing the resulting construct from said promoter, thereby producing a sequence tagged polyribonucleotide.

17. A method for producing a sequence tag from a polynucleotide, said method comprising:
   (a) digesting said polynucleotide with a type II restriction enzyme to produce a first cohesive end;
   (b) providing a promoter-linker cassette comprising an RNA polymerase promoter, a restriction site for a type IIs restriction enzyme and a second cohesive end which is complementary to said first cohesive end produced by said type II restriction enzyme, wherein said cassette is digested to produce said second cohesive end;
   (c) ligating the digested polynucleotide to the cassette;
   (d) digesting the ligated product of step (c) with said type IIs restriction enzyme;
   (e) blunting the ends of the product of the type IIs digestion;
   (f) circularizing the product of step (e);
   (g) digesting the circularized product with said type II restriction enzyme;
   (h) blunting the ends of the product of the type II digestion; and
   (i) transcribing the resulting construct from said promoter, thereby producing a sequence tagged polyribonucleotide.

\* \* \* \* \*